United States Patent [19]

Balestrieri et al.

[11] Patent Number: 5,409,839
[45] Date of Patent: Apr. 25, 1995

[54] METHOD OF TAGGING AND DETECTING DRUGS, CROPS, CHEMICAL COMPOUNDS AND CURRENCY WITH PERFLUOROCARBON TRACERS (PFT'S)

[75] Inventors: Giorgio Balestrieri, New York; Norman Kaish, Whitestone, both of N.Y.

[73] Assignee: International Electronic Technology Corp., Farmingdale, N.Y.

[21] Appl. No.: 146,256

[22] Filed: Nov. 1, 1993

[51] Int. Cl.$^6$ .................................. G01N 33/22
[52] U.S. Cl. ................................ 436/56; 436/27; 436/816; 436/901
[58] Field of Search ............... 436/27, 56, 816, 901

[56] References Cited

U.S. PATENT DOCUMENTS 4,256,038  3/1981  Dietz et al. .............. 102/28 R

OTHER PUBLICATIONS

R. N. Dietz, Commercial Applications of Perfluorocarbon Tracer (PFT) Technology, Jun., 1991, BNL 46265 (REv. Sep. 1991).
R. N. Dietz, et al., Description and Design of Perfluorcarbon Tracer (PFT) Analysis System, Nov. 1989, BNL-43731.
R. R. Draxler et al., Across North America Tracer Experiment (Anatex): Sampling and Analysis, Mar. 1991, BNL-46981.
Brookhaven National Laboratory, Project Proposal, A New Natural Gas Pipeline Leak Detection and Pinpointing Technology, Mar. 1, 1993.
R. N. Dietz et al., The Continously Operating Perfluorocarbon Sniffer (COPS) For The Detection of Clandestine Tagged Explosives, May 1990, BNL-28114.
Gilbert J. Ferber et al., Demonstration of Long-Range Atmospheric Tracer System Usin Perfluorcarbons, Apr. 1981, NOAA Technical Memorandum ERL ARL-101.
Gunnar I. Senum, et al., Final Report of the Evaluation of Vapor Taggants and Substrates for the Tagging of Blasting Caps, Mar. 1980, BNL 51232, Department of Energy and Environment, Sponsored by the Bureau of AT&F of the US Dept of Treasury, Under the Direction of the Aerospace Corporation.
Material News, Jul./Aug. 1990.

Primary Examiner—Lyle A. Alexander
Attorney, Agent, or Firm—Karl F. Milde, Jr.

[57] ABSTRACT

A method of tagging and detecting illicit drugs or paper currency is disclosed which comprises the steps of:
(a) applying a Perfluorocarbon Tracer (PFT) to the drugs or currency such that said PFT is released over a period of time as a vapor taggant; and
(b) subsequently detecting the presence of said vapor taggant, and therefore the drugs or currency.

21 Claims, No Drawings

METHOD OF TAGGING AND DETECTING DRUGS, CROPS, CHEMICAL COMPOUNDS AND CURRENCY WITH PERFLUOROCARBON TRACERS (PFT'S)

BACKGROUND OF THE INVENTION

The present invention relates to the use of the Perfluorocarbon Tracer (PFT) technology for the tagging and detection of illicit drugs, crops, chemical compounds, currency and other illicit drug-related materials.

Tracers are volatile compounds added to various substances for the purpose of tagging and tracking the course of that substance in the environment. The tracer vapors are detectable at very low levels, parts-per-trillion (pp $10^{12}$) or less. Such tracers have no impact on health or the environment and are economically practical in the tagging of substances such as air, gas, liquids, and even solids.

The U.S. Pat. Nos. 3,991,680 and 4,256,038 relate to methods of detecting small bombs to provide security against terrorist activities which can cause the destruction of civil aircraft in flight or detonate explosives in places where large groups of people congregate. These methods involve the tagging explosive materials such as blasting caps with a so-called "vapor taggant" which can be "sniffed" and detected by suitable equipment. The vapor taggant disclosed in the U.S. Pat. No. 3,991,680 is sulfur hexafloride ($SF_6$) absorbed in a fluoropolymer. The vapor taggant disclosed in the U.S. Pat. No. 4,256,038 is a Perfluorocarbon Tracer ("PFT") which includes one or a plurality of the following compositions: perfluorocycloalkanes such as perfluorodimethylcyclobutane (PDCB), perfluoromethylcyclohexane (PMCH), and perfluorodimethylcyclohexane (PDCH); perfluoroaromatics such as hexafluorobenzene (HGB), octafluorotoluene (OFT), decafluorobinphenyl (DFBP), decafluoroxylene (DFX), octafluoronaphthalene (OFN), and pentafluoropyridene (PFP), perfluoroalkanes such as perfluorohexane (PFH), perfluoropentane (PFPT), and perfluorooctane (PFO), and perfluorocycloalkenes such as decafluorocyclohexene (DFCH) and octafluorocyclopentene (OFCP).

The disclosures of the U.S. Pat. Nos. 3,991,680 and 4,256,038 are incorporated herein by reference.

As disclosed in these patents, the detection system for explosives consists of:

(1) "taggants" (for example, the Perfluorocarbon Tracers, or "PFT's") that give off detectable inert tracers when applied to materials; and (2) a sensing system capable of detecting tracer elements of PFT's in the atmosphere.

In addition to the PFT's noted in these patents, it has been discovered that the following PFT compositions are also particularly useful as taggants: pf-methylcyclopentane (PMCP); pf-1,2-dimethylcyclohexane (o-PDCH[1]); pf-1,3-dimethylcyclohexane (m-PDCH[1]); pf-1,4-dimethylcyclohexane (p-PDCH[1]) and pf-trimethylcyclohexanes (PTCH).

Of the PFT taggants listed above, the following six are particularly preferred: PMCH, PMCP, o-PDCH[1], m-PDCH[1], p-PDCH[1] and PTCH. Any five of these six compositions may be combined, as desired, to form a specific "cocktail"; i.e., a taggant that can be selectively detected and discriminated with respect to other taggants.

Taggant use involves the detection of inert gaseous vapors (in minor tracer quantities) that are emitted over time. As there are a plurality of separate tracers in the PFT family, each with its own "fingerprint", the PFTs can be combined in a range of combinations and concentrations, yielding thousands of discrete "signatures". This allows discrimination between various taggants and enables the individual detection of multiple products, or the tracking of individually tagged products to provide exact identification and location.

The Perfluorocarbon Tracer technology is the most sensitive of all tracer technologies because the ambient background levels of the routinely used PFTs are extremely low (in the range of parts per quadrillion-ppq). With this technology's instrumentation, PFTs can be measured down to those levels. The effectiveness of this technology is achieved both in terms of cost (very little PFT need be used) and detectibility (very small traces can be effectively detected). The PFT compounds, which are invisible and environmentally and biologically safe to use, as well as the PFT detecting instrumentation, are presently commercially available.

Various methods of detection have been demonstrated conclusively in numerous application projects for PFT's including indoor heating and ventilation studies, underground leak detection and long range atmospheric studies.

The following provides a simplified description of how the tracers are detected and analyzed, in order to understand the advantages of PFTs over other gaseous and non-gaseous tracers. The PFTs can be analyzed by gas chromatography wherein the constituents of an air sample are thermally absorbed from a sample tube and are injected into the carrier gas stream via a sample valve (in a building structure, multiple sampling tubes are run throughout the different regions of the building being monitored). Before entering the chromatography column, all the components are present as a "slug". After passing through the column, the constituents are physically separated to an extent that depends on the nature and conditions of the column.

The high affinity of PFTs for reaction with electrons also makes them some of the most sensitive compounds for detection in an Electronic Capture Detector (ECD), which is a small (0.1 to 0.2) Ml) reaction chamber containing an electron source. The cloud of electrons in the chamber is periodically collected, producing a current. When tracer molecules enter the cell, the reacted electrons cannot be collected. The resulting reduction in current is a measure of the PFT concentration.

However, the atmosphere contains many components, the concentrations of which exceed those of the PFTs and that are detectable in the ECD used to measure the PFTs. Included are $O_2$, nitrogen oxides, chlorofluorocarbons (CFCs), $SF_6$, and others, each of which could interfere with the early eluding PFTs. Physical means are used (e.g., sampling onto an absorbent with subsequent purging) to remove most of the oxygen and some of the CFC's. A catalyst bed operating at about 200° C. is needed to destroy many remaining interfering compounds so that the surviving PFTs can be detected.

Air sample collection is accomplished by several means. Inexpensive passive Capillary Absorption (sampling) Tubes (CATS), allow the monitoring of surveillance areas in remote or congested locations. These sampling tubes are collected and sent to a laboratory for analysis. Alternatively, a real time Continuously Operating Perfluorocarbon Sniffer (COPS) can provide immediate indications of the source of PFT emissions. Both the COPS and the ECD are commercially available.

It is the physical and chemical inertness of the PFTs that not only prevents their loss in the atmosphere, but also helps in their separation and analysis from less stable interfering compounds and makes them biologically inactive; and thus perfectly safe to use. Their limited industrial use not only results in low ambient background concentration, but also precludes the possibility of numerous higher local concentrations that might confuse detection capability.

PFT technology has already been developed and utilized in various applications including: (1) detection of leaks in underground storage tanks; (2) detection of leaks in high-pressure, oil-filled electric transmission lines; (3) atmospheric tracing and air pollution dispersion studies; (4) building ventilation studies and (5) detection of tagged explosives (blasting caps) in airline luggage. Investigation is underway for exploring the application of PFTs to the detection of leaks in natural gas pipelines and to early warning fire detection systems.

Effective inspection of large containers and trucks for controlled substances and narcotics is essential for the success of drug interdiction efforts. A significant fraction of drugs are smuggled through this avenue. Without prior knowledge provided through intelligence activities, the chances for drug detection are very slim. A successful drug interdiction program therefore requires efficient, rapid and cost-effective inspection techniques for large objects. The current technique used to thoroughly inspect containers is manual, highly labor intensive and can hardly be expanded to meet the challenge of abating the flow of illicit drugs from one country to another. Hence, the only way to achieve the goal of an effective counter-drug effort is to develop a rapid, automatic, non-intrusive inspection system to inspect shipments and cargo containers without removing all of the contents for manual inspection.

SUMMARY OF THE INVENTION

It is a principal object of the present invention to provide a method of detecting illicit drugs, crops, chemical compounds and currency with Perfluorocarbon Tracers (PFTs) as taggants for the identification and tracking of illicit drug-related materials, production facilities and activities.

These objects, as well as further object which will become apparent from the discussion that follows, are achieved, in accordance with the present invention, by a method comprising the steps of:
(a) applying a Perfluorocarbon Tracer (PFT) to the drugs or currency, such that said PFT is released over a period of time as a vapor taggant; and
(b) subsequently detecting the presence of said vapor taggant, and therefore the drugs or currency.

DESCRIPTION OF THE PREFERRED EMBODIMENTS

A. Tagging, Detecting and Tracing of Currency, Packages and Cargo

The application of the Perfluorocarbon Tracer (PFT) technology in the tagging, detecting and tracing of money, packages and cargo will entail the tagging of currency and packages (which might be used in, or be part of an illicit drug transaction) with a PFT taggant for the purposes of subsequent tracing and identification. The innovation of utilizing Perfluorocarbon Tracer (PFT) technology to provide a method for non-invasive detection of detecting currency, packaging and wrappers used in illicit drug trade rests with its most basic technological improvement over existing drug detection techniques. Sampling the environment for trace levels of drugs involves collecting samples that may contain hundreds and perhaps thousands of different compounds. By using a PFT it is necessary only to identify a single compound group.

The application of PFT's as a drug detection methodology will involve detection by crime fighting agents and/or customs or treasury field inspectors, and the application of the taggant material through covert agents or ongoing programs. Timely examination of containers, cargo and vehicles for contraband without the need for physical disassembly is a key component in the war against drugs. This non-intrusive inspection poses great technical challenges that stem from basic as well as operational issues. Perfluorocarbon Tracers offer capabilities which are essential to having effective detection devices. These are: high penetrability, high sensitivity, high specificity, high-speed, non-intrusiveness and possibilities for automatic decision making. The present invention thus allows agents to determine the presence or existence of pre-tagged money (paper currency) in packages under several different scenarios:
a) Tagging a selected shipment of money that may become involved in a drug transaction so that the currency can be detected without visual or intrusive inspection;
b) Tagging all or significant parts of the Federal currency to prevent the export of large quantities of cash which are often associated with major drug transactions; and
c) Tagging parcels and/or packaging; i.e., containers of illicit drug related materials (e.g., currency, chemicals, manufacturing equipment and drugs themselves) in order to discretely trace their movements.

This application of PFT's will enable Drug Enforcement Agency agents to "sniff" for the PFT vapor emissions in luggage containing currency used in drug transactions, as well as vehicles, containers and vessels in which drugs are being transported in a non-obtrusive manner.

A fundamental assumption which is made in trace contraband detection is that residues are present on the exterior surfaces of contraband. It has been confirmed, in the course of many field and laboratory studies, that detectable residues are indeed present in virtually all cases of contraband concealment in luggage. Hence, the primary task is to seek out and detect contraband residues in luggage or cargo surfaces, which in turn infers that the contaminated luggage contains bulk contraband.

The use of PFTs in this context would likely provide agents the ability to "identify" transport vehicles even if there is no contraband cargo in the box, due to the residual emissions of PFTs. Previously tagged cargo will build-up a steady state concentration of PFTs; those vapors can be reliably detected at the vented locations on transportation vehicles, and from luggage and/or other shipping containers, even if the contraband cargo has been removed.

Previous R&D has proven that the use of microencapsulation of PFTs can be useful for slow release in a tagged vehicle, container or package. Microcapsules with absorbed PFT's can be adhered to cargo and will remain relatively inconspicuous. For example, previous research has shown that Styrofoam boxes, suitcases, attaches and heat sealed plastic bags are all poor barriers of PFTs due to the relative lack of air tightness. Even aluminum luggage with rubber gaskets does not prevent the detection of a vapor taggant. Field experiments have verified theoretical models of barrier enclosed explosives. The result indicates the ability for real-time detection of taggants using a taggant detection with a parts-per-trillion level of detection and a sampling system having a dilution factor of 1000. Another conclusion of the model is that the taggant concentration obtained in a moderately sized room fifteen minutes following the introduction of a severe barrier containing a taggant source of one nano-liter/minute emission rate (placed in the room one hour earlier) is sufficient to allow detection by a concentration detection scheme. A moderate barrier, such as a suitcase or box would allow real-time continuous detection of luggage moving on a conveyor belt. With detectors that have a response time of approximately one second, this application is fully practical.

R&D originally conducted in the 1980s under sponsorship of the Bureau of Alcohol and Firearms of the U.S. Department of Treasury proved that PFTs were able to be micro-encapsulated for the purpose of tagging the blasting caps. This study concluded that vapor tagging of explosives for pre-detonation could be accomplished with the use of micro-encapsulated Perfluorocarbon Tracer chemical taggants. Taggant-containing microcapsules were found to be able to be blended into both the bulk explosives as well as in the labels and closures. Once incorporated into or on bulk substances, vapor taggants permeate the microcapsule membrane and provide a detectable and uniform source of taggant.

In this study, taggant containing microcapsules, manufactured by 3M, were examined. The capsule membrane material was a urea-formaldehyde polymer. The microcapsules were packed in tubing and then purged with $N_2$ to remove the released taggant for subsequent chromatographic analysis. Over a six month period, emission rates were found to be relatively constant.

B. Tagging and Detecting Processed or Final Product Drugs

The application of the Perfluorocarbon Tracer (PFT) technology in the tagging and detecting of processed or final product drugs can entail the tagging of crops by aerial spraying of fields or mixing finished or processed drugs with a taggant. Detection can take place by drug agents and/or customs field inspectors, and the taggant can be applied through covert agents or spraying crops in a manner similar to the crop eradication program which is currently in its final stages.

Additionally, detection of drug use in the body and body fluids is also possible. Drug detection instrumentation can deliver immediate or accurate results for the presence, amount and history of tagged drugs in the body, for example by breath detection upon exhaling.

In short, it is possible to apply the known PFT technology that has already been fully developed and used in other applications to detecting the presence of pre-tagged drug products during storage or shipment by truck, boat or airplane (i.e., pre-tagged drug cargo would emit detectable levels of PFTs from cargo holds or vents). This would allow agents to conduct a preliminary search of a suspected vehicle or vessel by "sniffing" for localized sources of PFT emissions.

Furthermore, the use of PFTs would likely provide agents the ability to "identify" transport vehicles even if there is no contraband cargo in the box, due to the residual emissions of PFTs.

The ability to detect PFTs within the body, while technically feasible, will require studies of the measurement of residual PFTs in the respiratory system.

Based on previous research demonstrated on a 727 aircraft, where a single stick of explosive, tagged with PFTs was detected through the rear outflow valve of the aircraft, it is known that tagged drugs will build up a steady state concentration of PFTs and that vapors will be reliably detected at the vented locations on transportation vehicles.

One method for the application of PFTs to illicit drugs is through "crop dusting" of drug precursors with insecticides containing PFT's. This method has a particularly good likelihood of success given the fact that:

(1) current airborne drug eradication techniques which include crop spraying/dusting are being phased out due to adverse environmental and economic impact on legal crop production; and (2) the prior experience with impregnating explosive blasting caps which demonstrated the ability to detect emissions from caps which have been previously "tagged" with micro-encapsulated PFTs.

The ability to impregnate a substrate (in this case, drug crops, packaged drugs, etc.) with PFTs and then being able to detect clandestine shipments at airport baggage handling areas provides a unique and unexpected "weapon" in the war on drugs.

C. Wide Area Surveillance of Illicit Botanical Laboratories and Other Processing Facilities The application of the Perfluorocarbon Tracer (PFT) technology in the tagging and detecting and wide area surveillance of botanical laboratories and other processing facilities entails the tagging of chemicals used in the processing of crops associated with the illicit drug trade. Detection could take place by airborne or land-based agents searching for these facilities in jungle and other sub-tropical, or highly congested urban areas. The taggant could be applied under law, by the manufacturers of the most commonly used additives, chemicals and solvents used in the drug trade. Based on previous research in the field, the viability for detecting tagged chemicals and laboratories utilizing them, both on the ground and through airborne (over flights of the suspected areas) and mobile sensors should prove highly successful.

Demonstrations and proof-of-concept tests have been conducted under Department of Energy contracts which have implications in a number of the environmentally-oriented and commercial applications. Specifically, under sponsorship from the National Oceanographic and Atmospheric Administration and the U.S. Environmental Protection Agency, recent demonstrations of the use of the PFT technology to provide accurate atmospheric tracing and air flow measurements across wide-areas of geography were conducted.

Additionally, an air dispersion test using PFTs was conducted in 1993 to identify the source of the haze over the Grand Canyon. Through the detection of the various PFTs releases from known sources of the pollution, the actual source was pinpointed at a power plant located over 100 miles down stream. In other experiments, tracer releases were made over a three month period with sampling out to distances of 3000 km at concentrations down to $0.5 \times 10^{-15}$ L/L of air.

The present invention has its scientific basis in work previously conducted during a Cross North America Tracer Experiment. During this experiment, three PFTs were released at an industrial park, both in "flatlands" devoid of vegetation and at sites where trees were 100 meters in height. At the release locations, the tracers were evaporated into a heated air stream through a stove pipe ending two meters above the roof of a one story building.

Aircraft were then used, each with the capability to automatically collect twenty air samples which were later sent to a laboratory for PFT analysis. In addition to the collected samples the aircraft was also equipped with a two-trap sampler, PFT analyzer for real time tracer plume detection. The plane flew at a speed of 250 Km/hour at 500-1500 feet.

Sampling usually occurred soon after the release of the PFTs, but for several night time releases during conditions of strong surface based inversions with light winds, sampling was delayed until the next day when the plume mixed high enough for aircraft sampling. The aircraft frequently flew perpendicular to the plume, back and forth along a line at the same or different altitudes. Based on study findings, PFT concentrations in the plume sampled from aircraft were typically two orders of magnitude greater than ground level samples.

The fixed ground and airborne sampling data, when coupled with known weather and atmospheric data, can provide the total picture leading to an accurate back track to the PFT emissions source.

In 1988, an experiment was conducted on the ground to detect a leak in a tagged natural gas line for a utility. Utilizing passive Capillary Absorption (sampling) Tubes mounted on telephone poles (POLE CATS), the underground leak was detected within one-half block by the passive tubes. When utilizing a continuously operating Perfluorocarbon Sniffer (COPS) the leak was pin-pointed to within a few feet. This specific experiment demonstrates the capability for urban and high density tagged chemical detection using conventional PFT sniffing equipment.

There has thus been shown and described a novel method of tagging and detecting illicit drugs, crops, chemical compounds and currency with perfluorocarbon tracers (PFT'S) which fulfills all the objects and advantages sought therefor. Many changes, modifications, variations and other uses and applications of the subject invention will, however, become apparent to those skilled in the art after considering this specification which discloses the preferred embodiments thereof. All such changes, modifications, variations and other uses and applications which do not depart from the spirit and scope of the invention are deemed to be covered by the invention, which is to be limited only by the claims which follow.

What is claimed is:

1. A method of tagging and detecting paper currency, said method comprising the steps of:
   (a) applying a Perfluorocarbon Tracer (PFT) to said currency such that said PFT is released from said currency over a period of time as a vapor taggant; and
   (b) subsequently detecting the presence of said vapor taggant, and therefore said currency.

2. The method defined in claim 1, wherein said PFT is selected from the group of compositions consisting of PMCH, PMCP, o-PDCH', m-PDCH', p-PDCH' and PTCH.

3. The method defined in claim 2, wherein said PFT is a mixture of two or more of said compositions of said group.

4. The method defined in claim 3, wherein said PFT is a mixture of two to five of said compositions of said group.

5. The method defined in claim 2, wherein said detecting step includes the step of selectively detecting specific ones of said compositions of said group.

6. The method defined in claim 1, wherein said applying step comprises the step of subjecting said currency to a PFT vapor.

7. The method defined in claim 1, wherein said applying step comprises the steps of:
   (1) dissolving a PFT in a liquid carrier; and
   (2) applying said liquid carrier with said dissolved PFT to said currency.

8. The method defined in claim 7, wherein said liquid carrier is an oil.

9. The method defined in claim 7, wherein said treating step of applying said carrier to said currency includes printing said carrier on said currency.

10. The method defined in claim 9, wherein said carrier is a substantially clear liquid.

11. The method defined in claim 1, wherein said applying step comprises the steps of:
    (1) encapsulating a PFT in a plurality of microcapsules; and
    (2) applying said microcapsules with said encapsulated PFT to said currency.

12. A method of tagging and detecting illicit drugs, said method comprising the steps of:
    (a) applying a Perfluorocarbon Tracer (PFT) to said drugs, such that said PFT is released from said drugs over a period of time as a vapor taggant; and
    (b) subsequently detecting the presence of said vapor taggant, and therefore said drugs.

13. The method defined in claim 12, wherein said applying step includes the steps of:
    (1) dissolving a PFT in a liquid carrier; and
    (2) treating a precursor required in the manufacture of said drugs to said liquid carrier with said dissolved PFT.

14. The method defined in claim 13, wherein said treating step includes the step of spraying crops which are used in the manufacture of illicit drugs with a liquid carrier with said dissolved PFT.

15. The method defined in claim 12, wherein said treating step includes the step of applying a PFT to a chemical composition which is used as a precursor in the manufacture of illicit drugs.

16. The method defined in claim 14, wherein said applying step includes the steps of:
    (1) encapsulating a PFT in a plurality of microcapsules; and
    (2) applying microcapsules with said encapsulated PFT to a precursor required in the manufacture of said drugs.

17. The method defined in claim 15, wherein said applying step includes the steps of:

(1) encapsulating a PFT in a plurality of microcapsules; and (2) applying microcapsules with said encapsulated PFT to a precursor required in the manufacture of said drugs.

18. A method of tagging and detecting illicit drugs, said method comprising the steps of:

(a) applying a Perfluorocarbon Tracer (PFT) to a container of illicit drug related material, such that said PFT is released from said container over a period of time as a vapor taggant; and (b) subsequently detecting the presence of said vapor taggant, and therefore said container.

19. The method defined in claim 18, wherein said applying step includes the steps of:

(1) dissolving a PFT in a liquid carrier; and (2) treating said container with said liquid carrier with said dissolved PFT.

20. The method defined in claim 19, wherein said applying step includes the steps of:

(1) encapsulating a PFT in a plurality of microcapsules; and (2) applying microcapsules with said encapsulated PFT to said container.

21. The method defined in claim 19, wherein said applying step includes the steps of:

(1) encapsulating a PFT in a plurality of microcapsules; and (2) applying microcapsules with said encapsulated PFT to said container.

* * * * *